United States Patent [19]

Hussain

[11] Patent Number: 4,929,775
[45] Date of Patent: May 29, 1990

[54] PROCESS FOR PREPARING BROMINATED PENTAERYTHRITOLS

[75] Inventor: Saadat Hussain, Baton Rouge, La.

[73] Assignee: Ethyl Corporation, Richmond, Va.

[21] Appl. No.: 358,591

[22] Filed: May 30, 1989

[51] Int. Cl.$^5$ .................... C07C 31/36; C07C 31/42
[52] U.S. Cl. .................... 568/844; 560/236; 560/264; 560/266
[58] Field of Search ............ 568/844; 560/236, 264, 560/266

[56] References Cited

U.S. PATENT DOCUMENTS

| | | | |
|---|---|---|---|
| 3,876,509 | 4/1975 | Davis et al. | 203/38 |
| 3,883,581 | 5/1975 | Davis et al. | 260/485 |
| 3,932,541 | 1/1976 | Davis et al. | 260/633 |
| 4,154,966 | 5/1979 | Weil | 568/844 |

OTHER PUBLICATIONS

Wawzonek et al., Organic Synthesis, vol. 38 (1958), pp. 68–70.

*Primary Examiner*—Mars: Howard T.
*Attorney, Agent, or Firm*—Edgar E. Speilman, Jr.

[57] ABSTRACT

This invention relates to a process for preparing high purity dibromoneopentyl glycol which comprises: (a) charging a vessel with pentaerythritol, a first portion of aqueous HBr and a catalyst; (b) maintaining the liquid contents in the vessel at a temperature from 80° C. to 130° C. for 1 to 3 hours; (c) adding a second portion of aqueous HBr to provide a total HBr to pentaerythritol molar ratio of 1:3 to 1:6; (d) after the foregoing aqueous HBr addition, raising the temperature of the liquid content of the vessel to 120° C. to 180° C.; and (e) sweeping the headspace of the vessel during at least (b), (c) and (d) with an inert gas and removing the sweep gas and any vapors formed during the process from the vessel.

7 Claims, No Drawings

PROCESS FOR PREPARING BROMINATED PENTAERYTHRITOLS

BACKGROUND OF THE INVENTION

This invention relates to a process for preparing a product predominant in brominated pentaerythritols, which product has good color.

Brominated pentaerythritols are recognized as excellent flame retardants for use in polyurethane-based formulations. The most commercially significant brominated pentaerythritol is dibromoneopentyl glycol (DBNPG).

The commercial production of DBNPG is generally in accordance with the processes described in U.S. 3,932,541 and U.S. 4,154,966. The '541 process produces a product which is predominant in DBNPG, but which can contain significant amounts of monobromopentaerythritol and/or tribromoneopentyl alcohol. In distinction, the '966 is said to produce a product which is essentially pure (98%) DBNPG. The 2% balance of this product is assumed to be mono- and tribromo-homologs of pentaerythritol.

Whatever process is used to prepare the brominated pentaerythritol predominate products, the process preferably is designed to yield a product which is white or at least off-white. Products which are dark in color are not desired by formulators as the color can adversely affect the appearance of an article made from the polyurethane-based formulation.

It is, therefore, an object of this invention to provide a process for producing a brominated pentaerythritol product which has good color, which process is simple in execution and does not necessitate the use of anhydrous HBr.

THE INVENTION This invention relates to a process for preparing a product which is predominate in brominated pentaerythritols and which has at least an off-white color. The process features:

charging a vessel with pentaerythritol, a first portion of aqueous HBr and a catalyst selected from the group consisting of mono- or di- carboxylic acids, their anhydrides, their esters and mixtures of two or more of such acids, anhydrides and esters;

after charging, maintaining the liquid contents of the vessel at a temperature within the range of from about 80° to about 130° C. for a period within the range of from about 1 to about 3 hours;

then adding a second portion of aqueous HBr to the vessel over a period of from about 0.5 to about 2 hours while maintaining the liquid contents of the vessel at a temperature within the range of from about 80° C. to about 130° C., the first portion and the second portion providing a mole ratio of HBr to pentaerythritol which is within the range of from about 1:3 to about 1:6;

after the addition of the second portion of aqueous HBr is at least substantially complete, raising the temperature of the liquid contents of the vessel to a temperature within the range of from about 120° C. to about 180° C. and maintaining such temperature for a period of at least 0.6 hours; and sweeping the headspace of the vessel with an inert gas at least during two temperature maintenance steps and during the addition of the second portion of aqueous HBr, and removing from the vessel the sweep gas and any vapors formed therein.

The brominated pentaerythritols produced by the process of this invention are those in which 1 to 3 of the hydroxyls of the starting pentaerythritol have been replaced with bromine. Generally, the brominated pentaerythritol product will contain at least two brominated pentaerythritol species having different degrees of bromination. A product having a mixture of monobromopentaerythritol (1 hydroxyl replaced by bromine), DBNPG (2 hydroxyls replaced by bromine) and tribromoneopentyl alcohol (3 hydroxyls replaced by bromine) is commonly obtained by the subject process. It is preferred that the product contain at least 80 wt.% DBNPG with the mono- and tri-bromo homologs being in about a 1 to 2 weight ratio with respect to one another.

The product produced by the process of this invention has at least an off-white color. The obtainment of this color is related to the maintenance of the 120° C. to 180° C. temperature of the vessel liquid contents after the last of the aqueous HBr has been added to the vessel, to the use of the sweep gas and to the removal of the sweep gas, vapors and entrained matter from the vessel. The examples hereinafter provided report on the color change of the product during this temperature maintenance period.

The aqueous HBr used in the process of this invention preferably contain at least 45 wt.% HBr. Commercially available aqueous HBr generally contains about 48 to 65 wt.% HBr and is preferred as a good quantity of HBr can be available for reaction without the concomitant need for a vessel of large volume. High HBr concentrations also favorably effect reaction rates.

The first portion of aqueous HBr should provide from about 30% to about 60%, preferably from about 40% to about 50%, of the total amount of HBr charged and added to the vessel.

The pentaerythritol used in this process is a well known compound and is available commercially. If it is desired to produce brominated pentaerythritols which have chlorine constituents, then either a chloro-substituted pentaerythritol can be used as the starting reactant or a mixture of aqueous HCl and HBr can be used.

The catalyst used is, as before noted, a mono- or di-carboxylic acid, their anhydrides, their esters or a mixture of two or more of such acids, anhydrides and esters. The catalyst may also be a halogenated derivative of such acids, anhydrides, and esters. Exemplary of useful catalysts are, acetic acid, adipic acid, propionic acid, hexanoic acid, butyric acid, chloroacetic acid, benzoic acid, succinic acid, caprylic acid, glutaric acid, lauric acid, phthalic anhydride, acetic anhydride, acetates of DBNPG, and the like. Preferred catalysts are those aliphatic mono- or di-carboxylic acids which contain from 2 to about 8 carbon atoms. Their anhydrides and esters are likewise preferred. Most highly preferred are acetic acid, adipic acid and acetates of DBNPG.

The amount of catalyst used in the process is generally from about 0.1 to about 2.0 moles of catalyst per mole of pentaerythritol charged to the reactor. It is preferred that from about 0.5 to about 1.5 mole catalyst be used per mole of pentaerythritol.

The order in which the pentaerythritol, catalyst and the first portion of aqueous HBr are charged to the vessel is not significant. After charging, the vessel liquid contents are warmed to a temperature within the range of from about 80° C. to about 130° C. and held within that range for a period between about 1 hours to about 3 hours. During this period, reaction between the HBr and pentaerythritol occurs.

Subsequent to the foregoing period, a second portion of aqueous HBr is added to the vessel. The addition period is preferably from about 0.5 to about 2 hours. This second portion provides the balance of the total HBr fed to the vessel.

The first and second portions of aqueous HBr should together provide a molar excess within the range of from about 50% to about 200%, over the stoichiometric amount needed to produce the particular brominated pentaerythritol desired. For example, if DBNPG is desired as the predominate brominated pentaerythritol, the stoichiometric amount of HBr will be 2 moles of HBr per mole of pentaerythritol originally charged. Thus, the total amount of HBr used by the process will be from about 3 to about 6 moles of HBr per mole of pentaerythritol. If the stoichiometric amount or only a small molar excess is used the process efficiency, based on yield, will be lower than that which is economically desirable. If the amount of HBr used is much above a 600% molar excess the product can have an undesirable color and/or the unstable tetrabromide homolog can be formed.

After the addition of the second portion of aqueous HBr is at least substantially complete, the vessel liquid contents are heated to a temperature within the range of from about 120° C. to about 180° C., and preferably to a temperature within the range of from about 140° C. to about 170° C. The temperature is maintained for a period within the range of from about 0.5 to about 2 hours. A preferred period is from about 0.5 to about 1 hour.

The vessel headspace is substantially continuously swept with an inert gas. The inert gas is preferably nitrogen. Other suitable gases are argon, helium, neon. Sweeping of the vessel headspace serves two main purposes. First, the sweep insures that the vessel headspace does not provide an oxidizing atmosphere over the vessel contents. Secondly, the sweep aids in the removal of vapors, e.g. water, HBr, $CH_3COBr$ and $BrCH_2COOH$, and any entrained solid and liquid matter, e.g. $CH_3COOH$, from the vessel. The vapors and matter are, during most of the total process period, emanating from the liquid contents of the vessel. The amount of sweep gas used is that amount which at least accomplishes these two purposes.

Along with the inert gas sweep there is a simultaneous removal of the inert gas, vapors and entrained matter from the vessel. These removed vapors can be later treated for recovery of valuable reagents therefrom, e.g. HBr.

As can be seen from the following Examples, G.C. analysis indicates the presence of acetates in the final product. These acetates are generally acetate esters of brominated pentaerythritols which are produced due to the use of the acetic acid catalyst. These acetate esters or, for that matter, the acid esters produced from the use of other catalysts of this invention, can be easily converted to brominated pentaerythritols by transesterification. To effect transesterification, a $C_1$ to $C_4$ alcohol, such as methanol, can be added to the reaction vessel after the addition of the second portion of aqueous HBr has been completed. This alcohol addition will cause a drop in the temperature of the liquid contents of the vessel, however, the raising of the vessel liquid content to the 120° C. to 180° C. temperature range, as required by step (d), will result in distillation and removal from the vessel of the methyl acetate transesterification product and any excess methanol. Generally, near complete transesterification can be accomplished by using from about 1 to about 10 moles, preferably from about 5 to about 6 moles of methanol, per mole of pentaerythritol originally charged to the vessel.

The process of this invention is preferably and most conveniently run at atmospheric pressure. However, sub- and super-atmospheric pressures can be used.

EXAMPLE I

A 500 ml resin-kettle was equipped with a mechanical stirrer, a thermometer, a therm-o-watch, a reflux condenser and a recycling type Barret-trap. The kettle was charged with 68.1g (0.5 mole) pentaerythritol, 100 ml (150.5g), aqueous 48% HBr and 45.0g (0.75 mole) glacial acetic acid. The liquid contents were heated to a temperature of 110° C. Throughout the entire procedure the headspace in the reactor was swept with nitrogen. Prior to reaching 110° C., the liquid contents of the kettle were seen to boil. The nitrogen sweep gas and vapor coming from the boiling contents were continuously removed from the kettle. The condensables in the sweep gas/vapor mix were collected and the volume measured. Also, the vapor temperature was monitored. After about 1 hour from the initiation of the procedure 72 ml (118.0g) 48% aqueous HBr was added to the kettle. The addition was carried out slowly and took a period of about 45 minutes. During the addition time, the temperature of the kettle liquid contents was maintained between 108° C. and 110° C. The total amount of aqueous HBr used in the procedure amounted to 268.5g, which is equivalent to 1.6 moles of anhydrous HBr and which is a 60% excess of HBr over the stoichiometric amount theoretically needed to produce DBNPG from the 0.5 mole of pentaerythritol originally charged. After the aqueous HBr addition had been completed, the temperature of the kettle liquid contents was slowly raised to about 140° C. Obtainment of the 140° C. temperature took approximately 1 hour. The 140° C. temperature was maintained for 15 minutes. After this time, heat was removed from the kettle and its contents were allowed to cool. It was noted that just prior to heat removal that there was no distillate being collected and that the vapor temperature was 35° C. The liquid contents of the kettle were colorless. When the contents were cooled to 85° C. an off-white solid material was seen. The contents did not smell of acetic acid. After reaching room temperature a solid material was recovered which weighed 125.0g. This gave a 95% yield based upon the original amount of pentaerythritol charged and assuming that the product was pure DBNPG. The material had a melting point of 80° C. to 94° C.

The product was subjected to gas chromatography (G.C.) analysis. The analysis was characterized by the following:

⅛ inch × 6.0 feet stainless steel column, packed with 20% SE-30 on Chrom WAW cured at 300° C. for 72 hours.

Conditions

| Conditions: | |
|---|---|
| Temp 1 = 140° C. | Time 1 = 5.0 min |
| Temp 2 = 250° C. | Rate = 6° C./min |
| | Area blank for 2.0 min to eliminate solvent |
| Flow = 20 ml/min | |

-continued

Retention time of components:
DBNPG = 16.7–16.9 min, tribro-
moneopentyl alcohol =
17.8–17.9 min, tetrabromonated
pentaerythritol =
18.6–18.7 min, and acetates =
19.6–20.8 min.

G.C. analysis showed the following for the product:
DBNPG=79.6 area %, tribromoneopentyl alcohol=7.4% and impurities=10.4-5 area %. The impurities had a retention time which was substantially identical to the retention time for the tetrabromonated pentaerythritol. However, it was not believed that the impurities were tetrabromonated pentaerythritol as it would be highly unlikely that the tetrabromonated pentaerythritol content would be greater than that of the tribromoneopentyl alcohol content.

The following observations were made during the procedure.

TABLE I

| Cumulative Time (min) | Kettle contents °C. | Vapor °C. | Condensate vol. collected, cumulative (ml) | Comments |
|---|---|---|---|---|
| 0 | 100° C. | 50° C. | 0 | |
| 12 | 110° C. | 80° C. | 10.0 ml | vapor started to condense |
| 20 | 110° C. | 80° C. | 24.0 ml (23.7 g) | moderate boil - contents yellow |
| 30 | 110° C. | 85° C. | 36.5 ml (36.6 g) | moderate boil - contents yellow |
| 45 | 110° C. | 84° C. | 53.0 ml (53.7 g) | moderate boil - contents yellow |
| 60 | 110° C. | 86° C. | 67.0 ml (68.6 g) | moderate boil - contents yellow |
| 75 | 110° C. | 85° C. | 80.0 ml (82.1 g) | addition of aqueous HBr started |
| 90 | 108° C. | 86° C. | 90.0 ml (92.9 g) | aqueous HBr continued to be added |
| 105 | 110° C. | 88° C. | 100.0 ml (103.* g) | aqueous HBr continued to be added |
| 120 | 110° C. | 88° C. | 108.0 ml (113.0 g) | addition of aqueous HBr complete |
| 135 | 108° C. | 88° C. | 117.0 ml (122.6 g) | contents light orange |
| 150 | 110° C. | 88° C. | 124.5 ml (133.6 g) | contents light orange |
| 165 | 115° C. | 99° C. | 138.0 ml (152.0 g) | temperature of the pot allowed to rise to 140° C. |
| 180 | 116° C. | 100° C. | 157.5 ml (178.6 g) | temperature of the pot allowed to rise to 140° C. |
| 195 | 120° C. | 101° C. | 177.0 ml (206.9 g) | temperature of the pot allowed to rise to 140° C. |
| 210 | 135° C. | 96° C. | 193.0 ml (229.4 g) | less vapor seen |
| 225 | 140° C. | 50° C. | 198.0 ml (235.5 g) | contents lighter in color |
| 240 | 140° C. | 35° C. | 198.0 ml (235.5 g) | heat shut off and contents allowed to cool |

EXAMPLE II

The same equipment used in Example I was used for this Example.

The kettle was charged with 68.1g (0.5 mole) pentaerythritol, 100 ml (151.0g) aqueous 48% HBr and 45.0g (0.75 mole) glacial acetic acid.

The liquid contents were treated and stirred under a nitrogen sweep at 110° C. with continuous removal of vapors. The vapors were removed from the kettle, condensed and removed as a distillate. The rate of distillation was maintained at 40-45 ml per hour. After 1.5 hours of distillate recovery, a second addition of 48% HBr (144.0g) was made over a period of 45 minutes while carrying out the distillation as before. The temperature of the liquid contents was maintained at 110° C. throughout the addition. When the addition of HBr was complete, the liquid contents were distilled for another hour and then the temperature of the liquid contents was allowed to rise to 145° C.–150° C. Once this temperature was reached, the liquid contents were held at this temperature for another 30 minutes. The kettle contents were then allowed to cool. A solid material started to form at 80° C. Upon cooling to room temperature, a light tan solid material was recovered from the kettle. The total weight of the solid material was 120.0g, which represents a 92% yield based upon the original amount of pentaerythritol charged. The solid material melted at 80° C.–90° C. G.C. analysis of the solid material showed the following composition:

| | (Area %) |
|---|---|
| Dibromoneopentyl glycol | 84.3% |
| Tribromoneopentyl alcohol | 5.3% |
| Brominated acetate of pentaerythritol | 7.8% |
| Other | 1.6 |

What is claimed:

1. A process for preparing a product predominate in brominated pentaerythritols, which process comprises:
    (a) charging a vessel with pentaerythritol, a first portion of aqueous HBr and a catalyst selected from the group consisting of mono- or di-carboxylic acids, their anhydrides, their esters and mixtures of two or more of such acids, anhydrides and esters;
    (b) after (a), maintaining the liquid contents of the vessel at a temperature within the range of from about 80° C. to about 130° C. for period within the range of from about 1 to about 3 hours;
    (c) after (b), adding a second portion of aqueous HBr to the vessel over a period of from about 0.5 to about 2 hours while maintaining the liquid contents of the vessel at a temperature within the range of from about 80° C. to about 130° C., the first portion and the second portion providing a mole ratio of pentaerythritol to HBr which is within the range of from about 1:3 to about 1:6;
    (d) after the addition of the second portion of aqueous HBr is at least substantially complete, raising the temperature of the liquid contents of the vessel to a temperature within the range of from about 120° C. to about 180° C. and maintaining such temperature for a period of at least 0.5 hours; and
    (e) during at least steps (b), (c), and (d), sweeping the headspace of the vessel with an inert gas and removing from the vessel the sweep gas and any vapors formed during the process.

2. The process of claim 1 wherein said catalyst is acetic acid.

3. The process of claim 1 wherein the temperature maintained in (d) is within the range from about 140° C. to about 170° C.

4. The process of claim 1 wherein the temperature maintenance time in (d) is within the range of from about 0.5 to about 2 hours.

5. The process of claim 1 wherein said aqueous HBr contains from about 40 to about 65 weight percent HBr based upon the total weight of the aqueous HBr.

6. The process of claim 1 wherein the first portion of aqueous HBr comprises from about 30 to about 60% of the total amount of aqueous HBr charged in (a) and added in (e).

7. The process of claim 1 wherein after (c) and prior to (d), from about 1 to about 10 moles of an alcohol are added to the vessel.

* * * * *